US010086033B2

(12) United States Patent
Dale et al.

(10) Patent No.: US 10,086,033 B2
(45) Date of Patent: Oct. 2, 2018

(54) TREATMENT OF PAIN (71) Applicant: INNOVATIVE HERBAL PRODUCTS (AUST) PTY LTD, Sydney, New South Wales (AU)

(72) Inventors: Michael J. Dale, Armidale (AU); Gregory J. Dale, Wahroonga (AU)

(73) Assignee: INNOVATIVE HERBAL PRODUCTS (AUST) PTY LTD, Sydney (AU)

( * ) Notice: Subject to any disclaimer, the term of this patent is extended or adjusted under 35 U.S.C. 154(b) by 0 days.

(21) Appl. No.: 15/107,494

(22) PCT Filed: Dec. 24, 2014

(86) PCT No.: PCT/AU2014/001164
§ 371 (c)(1),
(2) Date: Jun. 23, 2016

(87) PCT Pub. No.: WO2015/095918
PCT Pub. Date: Jul. 2, 2015

(65) Prior Publication Data
US 2016/0317599 A1 Nov. 3, 2016

(30) Foreign Application Priority Data
Dec. 24, 2013 (AU) ................. 2013905080

(51) Int. Cl.
*A61K 36/00* (2006.01)
*A61K 36/9068* (2006.01)
*A61K 9/00* (2006.01)
*A61K 31/12* (2006.01)

(52) U.S. Cl.
CPC ........ *A61K 36/9068* (2013.01); *A61K 9/0014* (2013.01); *A61K 31/12* (2013.01); *A61K 2236/00* (2013.01); *A61K 2236/17* (2013.01); *A61K 2236/37* (2013.01)

(58) Field of Classification Search
CPC ..................................... A61K 36/00
See application file for complete search history.

(56) References Cited

U.S. PATENT DOCUMENTS

| | | | |
|---|---|---|---|
| 6,312,736 B1 | 11/2001 | Kelly et al. | |
| 6,465,517 B1 | 10/2002 | Van Der | |
| 6,743,416 B2 | 6/2004 | Riedl | |
| 7,192,614 B2 | 3/2007 | Mitchell et al. | |
| 7,368,135 B1 | 5/2008 | Anderson et al. | |
| 2003/0035853 A1* | 2/2003 | Weidner ............. | A61K 36/9068 424/756 |
| 2004/0247705 A1 | 12/2004 | Roberts | |
| 2005/0031772 A1 | 2/2005 | Gaedcke et al. | |
| 2008/0317887 A1 | 12/2008 | Mitchell et al. | |
| 2011/0280976 A1 | 11/2011 | Castor et al. | |
| 2012/0148511 A1 | 6/2012 | Ijiri et al. | |
| 2013/0266672 A1* | 10/2013 | Bombardelli ........ | A61K 9/0014 424/737 |

FOREIGN PATENT DOCUMENTS

| | | | |
|---|---|---|---|
| CN | 101199830 A | * | 6/2008 |
| CN | 103127473 | | 6/2013 |
| JP | 61263909 | | 11/1986 |
| JP | 02135069 A | * | 5/1990 |
| WO | 2002080682 | | 10/2002 |
| WO | 2003045411 A2 | | 6/2003 |
| WO | 2008070783 A2 | | 6/2008 |
| WO | 2009055849 | | 5/2009 |
| WO | 2010062581 | | 6/2010 |
| WO | 2012013551 | | 2/2012 |
| WO | 2012026829 A1 | | 3/2012 |
| WO | 2013115456 | | 8/2013 |

OTHER PUBLICATIONS

International Patent Application No. PCT/AU2014/001164, "International Search Report", dated Feb. 18, 2015.
International Patent Application No. PCT/AU2014/001164, "Written Opinion", dated Feb. 18, 2015.
International Patent Application No. PCT/AU2014/001164, "International Preliminary Report on Patentability", dated Dec. 24, 2015.
Vedavathy , "Tribal medicine—The real alternative", Indian J Traditional Knowledge (2002): 25-31.
Dugasani et al., Comparative antioxidant and anti-inflammatory effects of [6]-gingerol, [8]-gingerol, [10]-gingerol and [6]-shogaol, Journal of Ethnopharmacology, vol. 127, 2010, pp. 515-520.
Emmanuel et al., Phytochemical screening, chemical composition and antimicrobial activity of Zingiber officinale essential oil of Adamaoua region (Cameroon), Journal of Chemical and Pharmaceutical Research, vol. 5, No. 7, 2013, pp. 296-301.
Ha et al., 6-Shogaol, a ginger product, modulates neuroinflammation: A new approach to neuroprotection, Neuropharmacology, vol. 63, 2012, pp. 211-223.
Jorge et al., Topical preparations for pain relief: efficacy and patient adherence, Journal of Pain Research, vol. 4, 2011, pp. 11-24.
Leal et al., Functional Properties of Spice Extracts Obtained via Supercritical Fluid Extraction, J. Agric. Food Chem., vol. 51, No. 9, American Chemical Society, 2003, pp. 2520-2525.
Lee , Liquid Chromatographic Determination of 6-, 8-, 10-Gingerol, and 6-Shogaol in Ginger (*Zingiber officinale*) as the Raw Herb and dried Aqueous Extract, Journal of AOAC International, vol. 90, No. 5, 2007, pp. 1219-1226.
Mustafa et al., Ginger (*Zingiber officinale*) in Migraine Headache, Journal of Ethnopharmacology, vol. 29, 1990, pp. 267-273.
Wohlmuth et al., Essential Oil Composition of Diploid and Tetraploid Clones of Ginger (*Zingiber officinale roscoe*) Grown in Australia, J. Agric. Food Chem., vol. 54, 2006, pp. 1414-1419.

(Continued)

*Primary Examiner* — Qiuwen Mi
(74) *Attorney, Agent, or Firm* — Kilpatrick Townsend & Stockton LLP (57) ABSTRACT

The invention relates to a method of treating or preventing pain, or a condition associated with pain, in a subject in need thereof comprising applying topically an effective amount of an extract of *Zingiber Officinale* (ginger), and to topical compositions and articles of manufacture comprising an extract of *Zingiber Officinale*.

12 Claims, 1 Drawing Sheet

(56) References Cited

OTHER PUBLICATIONS

Young et al., Analgesic and anti-inflammatory activities of [6]-gingerol, Journal of Ethnopharmacology, vol. 96, 2005, pp. 207-210.
Bartley et al., Supercritical Fluid Extraction of Australian-Grown Ginger (*Zingiber officinale*), Journal of the Science of Food and Agriculture, vol. 66, No. 3, Nov. 1, 1994, pp. 365-371.
European Patent Application No. 14873553.3, Extended European Search Report dated Oct. 12, 2017, 7 pages.
Dugasani et al., "Comparative antioxidant and anti-inflammatory effects of [6]-gingerol, [8]-gingerol, [10]-gingerol and [6]-shogaol", Journal of Ethnopharmacology, vol. 127, 2010, pp. 515-520.
Durham, "Calcitonin Gene-Related Peptide (CGRP) and Migraine", Headache, vol. 46, Jun. 2006, 9 Pages, S3-S8.
Slavin et al., "Impact of Food Components on in vitro Calcitonin Gene-Related Peptide Secretion—A Potential Mechanism for Dietary Influence on Migraine", Nutrients, vol. 8, 2016, 11 Pages.
Van Breemen et al., "Cyclooxygenase-2 inhibitors in ginger (*Zingiber officinale*)", Fitoterapia, vol. 82(1), Jan. 2011, pp. 38-43.

\* cited by examiner

TREATMENT OF PAIN

PRIOR RELATED APPLICATIONS

This application is a National Phase application of International Application No. PCT/AU2014/001164, filed Dec. 24, 2014, which claims priority to Australian Application No. 2013905080, filed Dec. 24, 2013, each of which is incorporated herein by reference in its entirety.

FIELD OF THE INVENTION

The present invention relates to a method for treating or preventing pain, and a composition for treating or preventing pain.

BACKGROUND

Pain is one of the most common reasons for physician consultation. Pain can interfere with a person's quality of life and general functioning.

One example of pain that has significant effects on a person's quality of life is migraine headache (migraine). Migraine is a chronic neurovascular disorder characterized by recurrent attacks of severe headache and autonomic nervous system dysfunction. Subjects suffering from migraine experience recurrent attacks of severe, pulsating and disabling headache, vomiting, photo- and phonophobia, and malaise. Approximately one third of migraine sufferers experience migraine with aura. An aura is a transient focal neurological phenomena that occurs before or during headache, and includes visual, sensory, language or motor disturbances.

The pathophysiology of migraine is only partly understood. In this regard, migraine appears to be associated with a wave of vasoconstriction followed by reactive vasodilation. The main elements involved in the generation of migraine pain are: cranial blood vessels, the trigeminal innervation of vessels and the reflex connections of the trigeminal systems with the cranial para-sympathetic outflow.

Treatment of pain, including migraine, consists of non-pharmacological and pharmacological approaches. Pharmacological treatment includes analgesics such as non-steroidal anti-inflammatory drugs (NSAIDS); triptans such as sumatriptan; ergotamines such as ergotamine and hydro ergotamine. However, ergotamines are associated with side-effects including hypotension, tiredness, increased weight and breathlessness, while triptans are associated with side-effects such as dizziness, heaviness or pressure on chest and arms, shortness of breath and chest pain.

Non-pharmacological therapies include acupuncture, oral administration of magnesium, co-enzyme, riboflavin, vitamin B, and/or various plant extracts.

There is a need for alternative therapies for the treatment of pain, such as migraine.

SUMMARY

A first aspect provides a method of treating or preventing pain, or a condition associated with pain, in a subject in need thereof, comprising applying topically an effective amount of an extract of *Zingiber Officinale* (ginger).

An alternative first aspect is the use of an extract of *Zingiber officinale* in the manufacture of a medicament for treating or preventing pain, or a condition associated with pain, in a subject in need thereof, wherein the medicament is for topical administration, or an extract of *Zingiber officinale* for use in treating or preventing pain, or a condition associated with pain, in a subject in need thereof, wherein the extract is for topical administration.

A second aspect provides a method of treating or preventing migraine, or a condition associated with migraine, in a subject in need thereof, comprising applying topically an effective amount of an extract of *Zingiber officinale*.

An alternative second aspect is the use of an extract of *Zingiber officinale* in the manufacture of a medicament for treating or preventing migraine, or a condition associated with migraine, in a subject in need thereof, wherein the medicament is for topical administration, or an extract of *Zingiber officinale* for use in treating or preventing migraine, or a condition associated with migraine, in a subject in need thereof, wherein the extract is for topical administration.

A third aspect provides a topical composition comprising an extract of *Zingiber officinale*.

A fourth aspect provides an article of manufacture comprising an extract of *Zingiber officinale* and a device for topical administration of the extract.

A fifth aspect provides a kit for treating or preventing pain or a condition associated with pain in a subject in need thereof comprising an extract of *Zingiber officinale* for topical administration.

A sixth aspect provides a topical composition comprising:
(a) one or more gingerols selected from the group consisting of 6-gingerol and 10-gingerol; and/or
(b) one or more gingerdiones selected from the group consisting of 6-gingerdione and 8-gingerdione; and/or
(c) one or more shogaols selected from the group consisting of 6-shogaol, 8-shogaol, and 10-shogaol,
and a pharmaceutically acceptable carrier.

A seventh aspect provides a method of treating or preventing pain, or a condition associated with pain, in a subject in need thereof, comprising applying an effective amount of a topical composition comprising:
(a) one or more gingerols selected from the group consisting of 6-gingerol and 10-gingerol; and/or
(b) one or more gingerdiones selected from the group consisting of 6-gingerdione and 8-gingerdione; and/or
(c) one or more shogaols selected from the group consisting of 6-shogaol, 8-shogaol, and 10-shogaol,
and a pharmaceutically acceptable carrier.

An alternative seventh aspect provides use of
(a) one or more gingerols selected from the group consisting of 6-gingerol and 10-gingerol; and/or
(b) one or more gingerdiones selected from the group consisting of 6-gingerdione and 8-gingerdione; and/or
(c) one or more shogaols selected from the group consisting of 6-shogaol, 8-shogaol, and 10-shogaol,
in the manufacture of a topical composition for treating or preventing pain, or a condition associated with pain, in a subject in need thereof, or a topical composition comprising:
(a) one or more gingerols selected from the group consisting of 6-gingerol and 10-gingerol; and/or
(b) one or more gingerdiones selected from the group consisting of 6-gingerdione and 8-gingerdione; and/or
(c) one or more shogaols selected from the group consisting of 6-shogaol, 8-shogaol, and 10-shogaol,
and a pharmaceutically acceptable carrier,
for use in treating or preventing pain, or a condition associated with pain, in a subject in need thereof.

An eighth aspect provides an article of manufacture comprising a topical composition comprising:
(a) one or more gingerols selected from the group consisting of 6-gingerol and 10-gingerol; and/or (b) one or more gingerdiones selected from the group consisting of 6-gingerdione and 8-gingerdione; and/or
(c) one or more shogaols selected from the group consisting of 6-shogaol, 8-shogaol, and 10-shogaol,
and a pharmaceutically acceptable carrier,
and a device for topical administration of the composition.

A ninth aspect provides a kit for treating or preventing pain, or a condition associated with pain, in a subject in need thereof comprising a topical composition comprising:
(a) one or more gingerols selected from the group consisting of 6-gingerol and 10-gingerol; and/or
(b) one or more gingerdiones selected from the group consisting of 6-gingerdione and 8-gingerdione; and/or
(c) one or more shogaols selected from the group consisting of 6-shogaol, 8-shogaol, and 10-shogaol,
and a pharmaceutically acceptable carrier.

A tenth aspect provides a method of treating or preventing pain, or a condition associated with pain, in a subject in need thereof, comprising applying topically an effective amount of a subcritical and/or supercritical $CO_2$ extract of *Zingiber officinale*.

An alternative tenth aspect is the use of a subcritical and/or supercritical $CO_2$ extract of *Zingiber officinale* in the manufacture of a medicament for treating or preventing pain, or a condition associated with pain, in a subject in need thereof, wherein the medicament is for topical administration, or a subcritical and/or supercritical $CO_2$ extract of *Zingiber officinale* for use in treating or preventing pain, or a condition associated with pain, in a subject in need thereof, wherein the extract is for topical administration.

An eleventh aspect provides a method of treating or preventing migraine, or a condition associated with migraine, in a subject in need thereof, comprising applying topically an effective amount of a subcritical and/or supercritical $CO_2$ extract of *Zingiber officinale*.

An alternative eleventh aspect is the use of a subcritical and/or supercritical $CO_2$ extract of *Zingiber officinale* in the manufacture of a medicament for treating or preventing migraine, or a condition associated with migraine, in a subject in need thereof, wherein the medicament is for topical administration, or a subcritical and/or supercritical $CO_2$ extract of *Zingiber officinale* for use in treating or preventing migraine, or a condition associated with migraine, in a subject in need thereof, wherein the extract is for topical administration.

A twelfth aspect provides a topical composition comprising a subcritical and/or supercritical $CO_2$ extract of *Zingiber officinale*.

A thirteenth aspect provides an article of manufacture comprising a subcritical and/or supercritical $CO_2$ extract of *Zingiber officinale* and a device for topical administration of the extract.

A fourteenth aspect provides a kit for treating or preventing pain, or a condition associated with pain, in a subject in need thereof comprising a topical composition comprising a subcritical and/or supercritical $CO_2$ extract of *Zingiber officinale*.

DETAILED DESCRIPTION

The present disclosure relates to the treatment and prevention of pain or conditions associated with pain.

The pain that can be treated by the method and composition as disclosed herein includes, for example, migraine, arthritis pain, menstrual pain, muscular pain. In one embodiment, the pain is migraine pain. In one embodiment, the migraine pain is migraine pain associated with aura. As used herein, "migraine pain associated with aura" is migraine which is preceded by, or occurs simultaneously with, an aura. An aura is a visual, sensory, language or motor disturbance which precedes the onset of, or occurs during, migraine headache. Visual disturbances may include, for example, scintillating scotoma and blurred vision. Sensory disturbances may include, for example, pins and needles in arms, hands, nose and/or mouth; vertigo, etc. In another embodiment, the pain is arthritis pain. In another embodiment, the pain is menstrual pain.

The inventors have found that topical administration of an extract of *Zingiber officinale* is effective at treating pain such as migraine. Topical application has the advantages that it is convenient and easy to apply rapidly, has less risk of toxicity and therefore offers a safer alternative to subjects concerned about side effects of oral medication. In addition, the reduction in treatment complexity increases the chance of patient compliance. The extract may also be used to treat or prevent conditions associated with pain. As used herein, a "condition associated with pain" is a condition which is caused by pain and/or occurs simultaneous with, or shortly before or after pain. Examples of such conditions include nausea, vomiting, photophobia, phonophobia, and malaise.

The method comprises applying topically, typically at or near the site of pain, an extract of *Zingiber officinale*. Typically, the extract is an extract of *Zingiber officinale* rhizome. In one embodiment, the extract of *Zingiber officinale* is an extract of dried *Zingiber officinale*.

In one embodiment, the extract of *Zingiber officinale* comprises one or more gingerols. Examples of gingerol include 6-gingerol, 8-gingerol, 10-gingerol and 12-gingerol. In one embodiment, the extract of *Zingiber officinale* comprises one or more shogaols. Examples of shogaols include 6-shogaol, 8-shogaol and 10-shogaol. In one embodiment, the extract of *Zingiber officinale* comprises one or more gingerdiones. Examples of gingerdiones include 6-gingerdione and 8-gingerdione. In one embodiment, the extract of *Zingiber officinale* comprises gingerdiol. Typically, the gingerdiol is 6-gingerdiol. In various embodiments, the extract of *Zingiber officinale* comprises:
(a) one or more gingerols and one or more shogaols;
(b) one or more gingerols and one or more gingerdiones;
(c) one or more shogaols and one or more gingerdiones;
(d) one or more gingerols, one or more shogaols and one or more gingerdiones.

In one embodiment, the amount of gingerols in the extract is in the range of from about 2% to 40%, 5% to 40%, 5% to 35%, 6% to 35%, 7% to 30%, 8% to 30%, 8% to 25%, weight per weight of extract.

In one embodiment, the amount of shogaol in the extract is in the range of from 0.3 to 7%, 0.3 to 6%, 0.3 to 5%, 0.4 to 5%, 0.4 to 4%, 0.5 to 4%, 0.7 to 4%, 0.8 to 3.5%, 0.9% to 3.0%, 1% to 3%, weight per weight of extract.

In one embodiment, the amount of gingerdiones in the extract is in the range of from about 0.2% to 10%, 0.3% to 10%, 0.5% to 10%, 0.6% to 10%, 0.7% to 10%, 0.8% to 10%, 0.9% to 10%, 1.0% to 10%, or 1.0% to 9%, weight per weight of extract.

In one embodiment, the extract comprises:
(a) one or more gingerols selected from the group consisting of 6-gingerol, 8-gingerol A, 8-gingerol B, 10-gingerol, and 12-gingerol;

(b) one or more gingerdiones selected from the group consisting of 6-gingerdione, 8-gingerdione; and
(c) one or more shogaols selected from the group consisting of 6-shogaol, 8-shogaol, and 10-shogaol.

In one embodiment, the extract comprises:
(a) one or more gingerols selected from the group consisting of 6-gingerol, 8-gingerol A, 8-gingerol B, 10-gingerol, and 12-gingerol;
(b) one or more gingerdiones selected from the group consisting of 6-gingerdione, 8-gingerdione; and
(c) one or more shogaols selected from the group consisting of 6-shogaol, 8-shogaol, and 10-shogaol; and
(d) 6-gingerdiol.

In various embodiments, the extract comprises:
(a) 6-gingerol;
(b) 6-gingerdione;
(c) 8-gingerdione;
(d) 10-gingerol;
(e) 6-shogaol;
(f) 10-shogaol;
(g) 6-gingerdiol;
(h) 6-gingerol, 6-gingerdione;
(i) 6-gingerol, 8-gingerdione;
(j) 6-gingerol, 10-gingerol,
(k) 6-gingerol, 6-gingerdione,
(l) 6-gingerol, 6-gingerdione, 8-gingerdione;
(m) 6-gingerol, 6-gingerdione, 10-gingerol;
(n) 6-gingerol, 6-gingerdione, 10-shogaol;
(o) 6-gingerol, 6-gingerdione, 6-gingerdiol;
(p) 6-gingerol, 6-gingerdione, 8-gingerdione, 10-gingerol;
(q) 6-gingerol, 6-gingerdione, 8-gingerdione, 10-shogaol;
(r) 6-gingerol, 6-gingerdione, 8-gingerdione, 6-gingerdiol;
(s) 6-gingerol, 6-gingerdione, 8-gingerdione, 10-shogaol;
(t) 6-gingerol, 8-gingerdione, 10-gingerol;
(u) 6-gingerol, 8-gingerdione, 10-shogaol;
(v) 6-gingerol, 8-gingerdione, 6-gingerdiol;
(w) 6-gingerol, 6-gingerdione, 8-gingerdione, 10-shogaol, 6-gingerdiol;
(x) 6-gingerol, 10-shogaol;
(y) 6-gingerol, 10-shogaol, 6-gingerdiol;
(z) 6-gingerol, 6-gingerdione, 10-gingerol, 8-gingerdione, 10-shogaol, 6-gingerdiol, 6-shogaol,
(aa) 6-gingerol, 6-gingerdione, 10-gingerol, 8-gingerdione, 10-shogaol, 6-gingerdiol, 6-shogaol, 8-gingerol A
(bb) 6-gingerol, 6-shogaol;
(cc) 6-gingerol, 6-shogaol, 6-gingerdione;
(dd) 6-gingerol, 6-shogaol, 8-gingerdione;
(ee) 6-gingerol, 6-shogaol, 6-gingerdione, 8-gingerdione;
(ff) 6-gingerol, 6-shogaol, 6-gingerdione, 8-gingerdione; 10-shogaol; or
(gg) 6-gingerol, 6-shogaol, 6-gingerdione, 8-gingerdione 10-shogaol, 6-gingerdiol.

In embodiments where the extract comprises 6-gingerol, the amount of 6-gingerol in the extract may, in some embodiments, be in the range of from about 2% to 40%, 5% to 40%, 6% to 35%, 7% to 30%, 8% to 30%, 9% to 25%, or 10% to 20%, weight per weight of extract.

In embodiments where the extract comprises 6-gingerdione, the amount of 6-gingerdione in the extract may, in some embodiments, be in the range of from about 0.2% to 10%, 0.2% to 8%, 0.2% to 7%, 0.3% to 6%, 0.3% to 5%, or 0.4% to 5%, weight per weight of extract.

In embodiments where the extract comprises 8-gingerdione, the amount of 8-gingerdione in the extract may, in some embodiments, be in the range of from about 0.02% to 10%, 0.05% to 8%, 0.1% to 7%, 0.2% to 6%, 0.3% to 6%, 0.4% to 6%, 0.5% to 6%, 0.6% to 6%, or 0.5% to 5%, weight per weight of extract.

In embodiments where the extract comprises 10-gingerol, the amount of 10-gingerol in the extract may, in some embodiments, be in the range of from about 0.15% to 10%, 0.2% to 9%, 0.3% to 8%, 0.4% to 7%, 0.5% to 7%, 0.6% to 7%, 0.71 to 7%, 0.8% to 7%, 0.9% to 7%, 1% to 7%, 1% to 6%, 1% to 5%, 1.5% to 5%, 2% to 5%, 2% to 6%, or 2% to 7%, weight per weight of extract.

In embodiments where the extract comprises 10-shogaol, the amount of 10-shogaol in the extract may, in some embodiments, be in the range of from about 0.04% to 3%, 0.04 to 2%, 0.05% to 2%, 0.06% to 2%, 0.1% to 1.5%, 0.2% to 1.5%, 0.06 to 1.5%, or 0.06% to 1%, weight per weight of extract.

In embodiments where the extract comprises 6-gingerdiol, the amount of 6-gingerdiol in the extract may, in some embodiments, be in the range of from about 0.25% to 5%, 0.25% to 4%, 0.25% to 3%, or 0.3% to 3%, weight per weight of extract.

In embodiments where the extract comprises 6-shogaol, the amount of 6-shogaol in the extract may, in some embodiments, be in the range of from about 0.2% to 10%, 0.25% to 9%, 0.3% to 8%, 0.4% to 7%, 0.5% to 6%, 0.6% to 5%, 0.7% to 5%, 0.2% to 5%, or 0.2 to 6%, weight per weight of extract.

In embodiments where the extract comprises 8-gingerol A, the amount of 8-gingerol A in the extract may, in some embodiments, be in the range of from about 0% to 10%, 0% to 8%, 0% to 7%, 0.01 to 6%, or 0.01% to 5%, weight per weight of extract.

In embodiments where the extract comprises 8-gingerol B, the amount of 8-gingerol B in the extract may, in some embodiments, be in the range of from about 0% to 10%, 0% to 8%, 0% to 7%, 0.01 to 6%, or 0.01% to 5%, weight per weight of extract.

In one embodiment, the amount of gingerols, gingerdiones and gingerdiols in the extract is in the range of from 2.5% to 50%, 5% to 50%, 10% to 50%, 15% to 50%, 15% to 45%, 15% to 40%, or 15% to 35%, weight per weight of extract.

In one embodiment, the amount of shogaols in the extract is in the range of from 0.3% to 7%, 0.3% to 6%, 0.3% to 5%, 0.4% to 5%, 0.4% to 4%, 0.5% to 4%, 0.7% to 4%, 0.8% to 3.5%, 0.9% to 3.0%, or 1% to 4%, weight per weight of extract.

The compounds 6-gingerol, 8-gingerol A, 8-gingerol B, 6-gingerdiol, 6-gingerdoine, 10-gingerol, 12-gingerol, 8-gingerdione, 6-shogaol, 8-shogaol, 10-shogaol, zingerone and 6-paradol are non-volatile compounds.

Typically, the extract of *Zingiber officinale* further comprises volatile compounds. As used herein, a "volatile compound" is a compound which has a vapour pressure that is greater than or equal to 0.001 kPa at 25° C. Typically, a volatile compound is volatized at room temperature. Volatile compounds in the extract of *Zingiber officinale* may include, for example, one or more of camphene, limonene, β-phellandrene, 1,8 cineole, linalool, borneol, α-terpineol, geraniol, neral, geranial, geranyl acetate, α-zingiberene, ar-curcumene, trans α-farnesene, β-bisabolene, trans muurola 4,5 diene, 1-sesquiphellandrene, and zingiberenol.

The inventors have found that extracts which exhibit greater efficacy for topical treatment of pain have an area percent ratio of volatile compounds to non-volatile compounds that is less than about 44.06. The "area percent" for a compound in a sample refers to the relative proportion of that compound expressed as a percentage of all compounds in the sample. The area percent of a compound is typically the area under a curve of a chromatogram that corresponds to that compound, expressed as a percentage of the total area under the curve of the chromatogram for the whole sample. Typically, the chromatogram is a chromatogram from gas chromatography. Typically, the gas chromatography is with a flame ionization detector (GCFID). Methods for GCFID and determining the area under the curve for components in a sample are known in the art. Methods for GC, including GCFID, are described in, for example, Harris, D. C. (1999) "24. Gas Chromatography." Quantitative Chemical Analysis (Fifth ed.). Freeman and Company; Grob, R. L and E. F. Barry (2004). Modern Practice of Gas Chromatography (4$^{th}$ Edition). John Wiley & Sons.

The area percent ratio of volatile compounds to non-volatile compounds in a sample is the area percent for volatile compounds in the sample divided by the area percent for non-volatile compounds in the sample.

In one embodiment, the area percent of volatile compounds is the area percent of the compounds camphene, limonene, β-phellandrene, 1,8 cineole, linalool, borneol, α-terpineol, geraniol, neral, geranial, geranyl acetate, α-zingiberene, ar-curcumene, trans α-farnesene, β-bisabolene, trans muurola 4,5 diene, β-sesquiphellandrene, and zingiberenol.

In one embodiment, the area percent of non-volatile compounds is the area percent of the compounds 6-gingerol, 8-gingerol A, 8-gingerol B, 6-gingerdiol, 6-gingerdoine, 10-gingerol, 12-gingerol, 8-gingerdione, 6-shogaol, 8-shogoal, 10-shogaol, zingerone and 6-paradol.

The inventors have found that an extract having a volatile to non-volatile area % ratio of 44.06 following GCFID has low efficacy in topical treatment of pain, and that extracts having a volatile to non-volatile area % ratio of 0.16 following GCFID are corrosive to the skin. The inventors have found that extracts having the greatest efficacy in the topical treatment of pain have a volatile to non-volatile area % ratio in the range of from 0.02 to 44, typically in the range of from 2 to 20, more typically in the range of 3.0 to 15.

In one embodiment, the extract comprises an area % ratio of volatile to non-volatile compounds in the range of from 0.02 to 44.0, 0.1 to 44.0, 0.2 to 44.0, 0.02 to 40.0, 0.1 to 40.0, 0.5 to 40.0, 0.02 to 35, 0.05 to 35.0, 0.1 to 35.0, 1.0 to 35.0, 0.05 to 30.0, 0.1 to 30.0, 1.0 to 30.0, 0.05 to 25.0, 0.1 to 25.0, 0.5 to 25.0, 1.0 to 25.0, 0.05 to 20.0, 0.1 to 20.0, 0.5 to 20.0, 1.0 to 20.0, 0.05 to 18.0, 0.1 to 18.0, 0.5 to 18.0, 1.0 to 18.0, 0.05 to 15.0, 0.1 to 15.0, 0.5 to 15.0, 1.0 to 15.0, 2.0 to 40.0, 2.0 to 35.0, 2.0 to 30.0, 2.0 to 25.0, 2.0 to 20.0, 2.0 to 15.0, 3.0 to 40.0, 3.0 to 35.0, 3.0 to 30.0, 3.0 to 25.0, 3.0 to 20.0, or 3.0 to 15.0. Typically, the area % is as determined by GCFID.

In one embodiment, the extract of *Zingiber officinale* comprises:
 (a) gingerols, gingerdiones and gingerdiols in an amount in the range of from 2.5% to 50%, 5% to 50%, 10% to 50%, 15% to 50%, 15% to 45%, 15% to 40%, or 15% to 35%, weight per weight of extract; (b) shogaols in an amount in the range of from 0.31 to 7%, 0.3% to 6%, 0.3% to 5%, 0.4% to 5%, 0.4% to 4%, 0.5% to 4%, 0.7% to 4%, 0.8% to 3.5%, 0.9% to 3.0%, or 1% to 4%, weight per weight; and
 (c) volatile and non-volatile compounds in an amount to give an area % ratio of volatile compounds to non-volatile compounds in the range of from 0.02 to 44.0, 0.1 to 44.0, 0.2 to 44.0, 0.02 to 40.0, 0.1 to 40.0, 0.5 to 40.0, 0.02 to 35, 0.05 to 35.0, 0.1 to 35.0, 1.0 to 35.0, 0.05 to 30.0, 0.1 to 30.0, 1.0 to 30.0, 0.05 to 25.0, 0.1 to 25.0, 0.5 to 25.0, 1.0 to 25.0, 0.05 to 20.0, 0.1 to 20.0, 0.5 to 20.0, 1.0 to 20.0, 0.05 to 18.0, 0.1 to 18.0, 0.5 to 18.0, 1.0 to 18.0, 0.05 to 15.0, 0.1 to 15.0, 0.5 to 15.0, 1.0 to 15.0, 2.0 to 40.0, 2.0 to 35.0, 2.0 to 30.0, 2.0 to 25.0, 2.0 to 20.0, 2.0 to 15.0, 3.0 to 40.0, 3.0 to 35.0, 3.0 to 30.0, 3.0 to 25.0, 3.0 to 20.0, or 3.0 to 15.0. Typically the area % is as determined by GC-FID.

In one embodiment, the extract of *Zingiber officinale* comprises:
 (a) gingerols, gingerdiones and gingerdiols in an amount to give an area % in the range of from 0.04 to 2, 0.04 to 1.8, 0.04 to 1.5, 0.1 to 1.5;
 (b) shogaols in an amount to give an area % in the range of from 0.90 to 20, 0.94 to 18, 0.94 to 16, 0.94 to 15, 0.94 to 14, 1.0 to 13, 1.5 to 13, 2.0 to 13, 2.5 to 13, 3.0 to 13, 3.5 to 13, 3.0 to 14, 3.0 to 15, 3.0 to 16; and
 (c) volatile and non-volatile compounds in an amount to give an area % ratio of volatile compounds to non-volatile compounds in the range of from 0.02 to 44.0, 0.1 to 44.0, 0.2 to 44.0, 0.02 to 40.0, 0.1 to 40.0, 0.5 to 40.0, 0.02 to 35, 0.05 to 35.0, 0.1 to 35.0, 1.0 to 35.0, 0.05 to 30.0, 0.1 to 30.0, 1.0 to 30.0, 0.05 to 25.0, 0.1 to 25.0, 0.5 to 25.0, 1.0 to 25.0, 0.05 to 20.0, 0.1 to 20.0, 0.5 to 20.0, 1.0 to 20.0, 0.05 to 18.0, 0.1 to 18.0, 0.5 to 18.0, 1.0 to 18.0, 0.05 to 15.0, 0.1 to 15.0, 0.5 to 15.0, 1.0 to 15.0, 2.0 to 40.0, 2.0 to 35.0, 2.0 to 30.0, 2.0 to 25.0, 2.0 to 20.0, 2.0 to 15.0, 3.0 to 40.0, 3.0 to 35.0, 3.0 to 30.0, 3.0 to 25.0, 3.0 to 20.0, or 3.0 to 15.0.

Typically the area % is as determined by GCFID.

In one embodiment, the volatile compounds are one or more compounds selected from the group consisting of camphene, limonene, β-phellandrene, 1,8 cineole, linalool, borneol, α-terpineol, geraniol, neral, geranial, geranyl acetate, α-zingiberene, ar-curcumene, trans, trans α-farnesene, β-bisabolene, trans muurola 4,5 diene, β-sesquiphellandrene, and zingiberenol.

In one embodiment, the area percent of volatile compounds is the area percent of the compounds camphene, limonene, β-phellandrene, 1,8 cineole, linalool, borneol, α-terpineol, geraniol, neral, geranial, geranyl acetate, α-zingiberene, ar-curcumene, trans α-farnesene, β-bisabolene, trans muurola 4,5 diene, β-sesquiphellandrene, and zingiberenol.

In one embodiment, the area percent of non-volatile compounds is the area percent of the compounds 6-gingerol, 8-gingerol A, 8-gingerol B, 6-gingerdiol, 6-gingerdoine, 10-gingerol, 12-gingerol, 8-gingerdione, 6-shogaol, 8-shogaol, 10-shogaol, zingerone and 6-paradol.

In one embodiment, the extract comprises 6-paradol. In embodiments where the extract comprises 6-paradol, the amount of 6-paradol in the extract may, in some embodiments, be in the range of from about 0.05% to 3%, 0.05% to 2.5%, 0.05% to 2%, 0.05% to 1.5%, 0.05% to 1.4%, or 0.05% to 1.3%, area % of the extract.

In one embodiment, the extract comprises zingerone. In embodiments where the extract comprises zingerone, the amount of zingerone in the extract may, in some embodiments, be in the range of from about 0.1% to 1.5%, 0.1% to 1.3%, 0.1 to 1.2%, 0.2 to 1.2% area % of the extract.

The extract may be prepared by extraction processes known in the art. In one embodiment, the extract is a solvent extract. An example of a solvent suitable for preparing the extract is a supercritical or subcritical gas. As used herein, a "supercritical gas" is a gas at supercritical temperature and pressure. A "subcritical gas" is a gas at subcritical temperature and pressure.

The subcritical temperature and pressure is the temperature and pressure at which the gas is not supercritical. A gas becomes supercritical when its temperature and pressure are above its critical point (i.e. where distinct liquid and gas phases do not exist, and/or at which no phase boundaries exist).

In one embodiment, the extract is a subcritical gas extract of *Zingiber officinale*. Typically, the subcritical gas extract of *Zingiber officinale* is a subcritical $CO_2$ extract of *Zingiber officinale*. The inventors have found that extracts, such as subcritical and supercritical $CO_2$ extracts, of *Zingiber officinale* are effective at treating pain following topical application at or near the site of pain. As used herein, a "subcritical gas extract" is an extract prepared by treating a material with a gas at subcritical temperature and pressure. It will be appreciated by those skilled in the art that a gas at subcritical temperature and pressure will typically be a liquid. Subcritical temperature and pressure will vary depending on the type of gas used. In embodiments in which the gas is $CO_2$, the subcritical temperature is typically in the range from 12'C to 31° C., more typically 15° C. to 31° C., still more typically 20'C to 30° C., still more typically 24'C to 29° C., still more typically 25° C. to 28° C. It will be appreciated by those skilled in the art that subcritical conditions may be maintained at temperatures higher than 31° C. by maintaining the pressure to below 1100 psi.

Typical subcritical pressures range from 800 to 1500 psi (5.51 MPa to 10.35 MPa), such as from 800 (5.51 MPa) to 1100 psi (7.58 MPa), 900 psi (6.21 MPa) to 1000 psi (6.90 MPa), 940 psi (6.48 MPa) to 990 psi (6.83 MPa), 941 psi (6.49 MPa) to 990 psi (6.83 MPa), or 942 psi (6.5 MPa) to 986 psi (6.8 MPa). It will be appreciated by those skilled in the art that subcritical conditions may be maintained at CO; pressures higher than 1100 psi by maintaining the temperature below 31.1° C.

Subcritical gas extraction typically involves pumping gas, such as $CO_2$, at a temperature of from 12° C. to 31° C. and a pressure of from 800 to 1500 psi through the plant material.

In another embodiment, the extract of *Zingiber officinale* is a supercritical gas extract of *Zingiber officinale*. As used herein, a "supercritical gas extract" is an extract prepared by treating a material with a gas at supercritical temperature and pressure. Supercritical temperature and pressure will vary depending on the type of gas used. Typically, the supercritical gas extract of *Zingiber officinale* is a supercritical $CO_2$ extract of *Zingiber officinale*. In embodiments in which the gas is $CO_2$, the supercritical temperature is above 31.1° C. and the supercritical pressure is above 1100 psi. Thus, supercritical extraction involves heating the gas, such as $CO_2$, to above 31.1° C. (87° F.) and pumping it through the plant material at about 1100 psi or above.

In some embodiments in which the gas is $CO_2$, the extraction is carried out at a temperature in the range of from 20'C to 50° C., 20° C. to 45° C., 20° C. (293.15K) to 40° C. (313.15K), 25° C. to 40° C., 30° C. to 40° C., 35° C. to 45° C., 35° C. to 40° C., 38° C. to 42° C., or 38° C. to 40° C.

In some embodiments in which the gas is $CO_2$, the extraction is carried out at a pressure in the range of from 800 psi (5.51 MPa) to 3000 psi (20.68 Mp), 1000 psi (6.9 MPa) to 3000 psi, 1100 psi (7.6 MPa) to 3000 psi (20.68 MPa), 1500 psi (10.34 MPa) to 3000 psi (20.68 MPa), 2000 psi (13.79 MPa) to 3000 psi (20.68 MPa), 2500 psi (17.24 MPa) to 3000 psi (20.68 MPa), 2800 psi (19.31 MPa) to 3000 psi (20.68 MPa). In one embodiment, the pressure is 2900 psi (20 MPa).

Methods for the preparation of subcritical and supercritical gas extracts of plant material are known in the art and are described in, for example, Int. J. Chem. Sci.: 8(2) (2010), pp. 729-743; WO09/055849.

In one embodiment, the *Zingiber officinale* is dried. Drying of *Zingiber officinale* results in production of shogaol from gingerols. On dehydration of *Zingiber Officinale*, gingerols lose a molecule of water to form the corresponding shogaols. Thus, extracts of dried *Zingiber officinale* have higher levels of shogaol than extracts of fresh *Zingiber officinale*. Without wishing to be bound by theory, the inventors believe that the presence of shogaol improves topical efficacy of the extract. Without wishing to be bound by theory, the inventors believe there is a synergy created by the combination of shogaols and gingerols in the extract which results in an efficacious extract. Dehydration of 6-gingerol to 6-shogaol is also favoured at high drying temperatures and acidic pH.

In one embodiment, the method of treating or preventing pain or a condition associated with pain comprises applying topically an extract of *Zingiber officinale* as described herein.

As used herein, "applying topically" refers to application to the skin. Typically the application to the skin is at or near the site of pain. The inventors have found that topical application of *Zingiber officinale* extract at or near the site of pain can effectively relieve pain, including difficult to treat pain such as migraine. As described herein, topical application of an extract of *Zingiber officinale* to the forehead and/or neck area of migraine sufferers resulted in relief of migraine pain, typically within 1 hour of its application.

Further, the inventors have found that topical application of the extract of *Zingiber officinale* at the first indications of onset of a migraine, such as for example, neck stiffness, aura (such as visual disturbances, pins and needles sensations), at a site on the head or neck or where the first indications are experienced, can reduce the severity of the migraine or prevent onset of the migraine.

The extract of *Zingiber officinale* can be applied topically to any portion of the body which results in pain relief. For migraine headaches, the extract can be applied to the forehead and/or other parts of the face, the neck, and/or the site at which first indications of onset of a migraine occur.

The extract of *Zingiber officinale* is applied topically. The present invention therefore provides a topical composition comprising an extract of *Zingiber officinale*. In one embodiment, the extract of *Zingiber officinale* is a solvent extract of *Zingiber officinale*. Typically, the solvent is $CO_2$. In one embodiment, the extract of *Zingiber officinale* is a subcritical gas extract of *Zingiber officinale*. In another embodiment, the extract of *Zingiber officinale* is a supercritical gas extract of *Zingiber officinale*. In one embodiment, the subcritical gas extract of *Zingiber officinale* is a subcritical $CO_2$ extract of *Zingiber officinale*. In one embodiment, the supercritical gas extract of *Zingiber officinale* is a supercritical $CO_2$ extract of *Zingiber officinale*.

The topical composition comprising an extract of *Zingiber officinale* may contain the extract as the sole component, or the composition may comprise other components. In one embodiment, the extract of *Zingiber officinale* is the only active ingredient in the composition. In one embodiment, the composition consists of the extract of *Zingiber officinale*. In various embodiments, the composition comprises from 50-100% extract of *Zingiber officinale*, 60-100% extract of *Zingiber officinale*, 70-100% extract of *Zingiber officinale*, 80-100% extract of *Zingiber officinale*, 90-100% extract of *Zingiber officinale*, 95-100% extract of *Zingiber officinale*, 98-100% extract of *Zingiber officinale*, 99-100% extract of *Zingiber officinale*. In one embodiment, the topical composition comprises 100% extract of *Zingiber officinale*.

The composition may comprise the extract of *Zingiber officinale* on its own, or formulated with any pharmaceutically acceptable carrier, provided the carrier does not adversely affect the efficacy of the extract. As used herein, "pharmaceutically acceptable" refers to a substance which does not interfere with the effectiveness of the biological activity of the active ingredients and which is not toxic to the subject. The suitability of the carrier for formulation of the composition can be readily tested by those skilled in the art. Suitable carriers include: low molecular weight peptides such as hydrolysates of wheat or other plant material, amino acids, emulsions such as oil-in-water, water-in-oil, and water-in-oil-in water emulsions; anhydrous liquid solvents such as oils (e.g. mineral oil), alcohols (e.g. ethanol, isopropanol), silicones (e.g. dimethicone, cyclomethicone).

The inventors envisage that topical compositions can be formulated from the components of the extract of *Zingiber officinale* described herein in isolated or purified form. Thus, the invention also provides a topical composition comprising one or more gingerols, one or more shogaols and/or one or more gingerdiones.

In various embodiments, the topical composition comprises:
(a) one or more gingerols and one or more shogaols;
(b) one or more gingerols and one or more gingerdiones;
(c) one or more shogaols and one or more gingerdiones;
(d) one or more gingerols, one or more shogaols and one or more gingerdiones.

In one embodiment, the topical composition comprises:
(a) one or more gingerols selected from the group consisting of 6-gingerol and 10-gingerol; and/or
(b) one or more gingerdiones selected from the group consisting of 6-gingerdione, 8-gingerdione; and/or
(c) one or more shogaols selected from the group consisting of 6-shogaol, 8-shogaol, and 10-shogaol.

In one embodiment, the topical composition comprises:
(a) one or more gingerols selected from the group consisting of 6-gingerol and 10-gingerol;
(b) one or more gingerdiones selected from the group consisting of 6-gingerdione, 8-gingerdione;
(c) one or more shogaols selected from the group consisting of 6-shogaol, 8-shogaol, and 10-shogaol; and
(d) 6-gingerdiol.

In one embodiment, the topical composition comprises:
(a) one or more gingerols selected from the group consisting of 6-gingerol, 8-gingerol A, 8-gingerol B, 10-gingerol, and 12-gingerol;
(b) one or more gingerdiones selected from the group consisting of 6-gingerdione, 8-gingerdione; and
(c) one or more shogaols selected from the group consisting of 6-shogaol, 8-shogaol, and 10-shogaol.

In one embodiment, the extract comprises:
(a) one or more gingerols selected from the group consisting of 6-gingerol, 8-gingerol A, 8-gingerol B, 10-gingerol, and 12-gingerol;
(b) one or more gingerdiones selected from the group consisting of 6-gingerdione, 8-gingerdione;
(c) one or more shogaols selected from the group consisting of 6-shogaol, 8-shogaol, and 10-shogaol; and
(d) 6-gingerdiol.

In various embodiments, the topical composition comprises:
(a) 6-gingerol;
(b) 6-gingerdione;
(c) 8-gingerdione;
(d) 10-gingerol;
(e) 6-shogaol;
(f) 10-shogaol;
(g) 6-gingerdiol;
(h) 6-gingerol, 6-gingerdione;
(i) 6-gingerol, 8-gingerdione;
(j) 6-gingerol, 10-gingerol;
(k) 6-gingerol, 6-gingerdiol;
(l) 6-gingerol, 6-gingerdione, 8-gingerdione;
(m) 6-gingerol, 6-gingerdione, 10-gingerol;
(n) 6-gingerol, 6-gingerdione, 10-shogaol;
(o) 6-gingerol, 6-gingerdione, 6-gingerdiol;
(p) 6-gingerol, 6-gingerdione, 8-gingerdione, 10-gingerol;
(q) 6-gingerol, 6-gingerdione, 8-gingerdione, 10-shogaol;
(r) 6-gingerol, 6-gingerdione, 8-gingerdione, 6-gingerdiol;
(s) 6-gingerol, 6-gingerdione, 8-gingerdione, 10-shogaol;
(t) 6-gingerol, 8-gingerdione, 10-gingerol;
(u) 6-gingerol, 8-gingerdione, 10-shogaol;
(v) 6-gingerol, 8-gingerdione, 6-gingerdiol;
(w) 6-gingerol, 6-gingerdione, 8-gingerdione, 10-shogaol, 6-gingerdiol;
(x) 6-gingerol, 10-shogaol;
(y) 6-gingerol, 10-shogaol, 6-gingerdiol;
(z) 6-gingerol, 6-gingerdione, 10-gingerol, 8-gingerdione, 10-shogaol, 6-gingerdiol, 6-shogaol;
(aa) 6-gingerol, 6-gingerdione, 10-gingerol, 8-gingerdione, 10-shogaol, 6-gingerdiol, 6-shogaol, 8-gingerol A;
(bb) 6-gingerol, 6-shogaol;
(cc) 6-gingerol, 6-shogaol, 6-gingerdione;
(dd) 6-gingerol, 6-shogaol, 8-gingerdione;
(ee) 6-gingerol, 6-shogaol, 6-gingerdione, 8-gingerdione;
(hh) 6-gingerol, 6-shogaol, 6-gingerdione, 8-gingerdione; 10-shogaol; or
(ff) 6-gingerol, 6-shogaol, 6-gingerdione, 8-gingerdione 10-shogaol, 6-gingerdiol.

In one embodiment, the amount of gingerols in the composition may be in the range of from about 2% to 40%, 5% to 40%, 6% to 35%, 7% to 30%, 8% to 30%, 8% to 25% weight per weight of composition.

In one embodiment, the amount of shogaol in the composition may be in the range of from 0.3 to 5%, 0.4 to 4%, 0.5 to 4%, 0.6% to 4%, 0.7% to 4%, 0.8% to 3.5%, 0.9% to 3.0%, or 1% to 3% weight per weight of composition.

In one embodiment, the amount of gingerdiones in the composition is in the range of from about 0.2% to 10%, 0.3% to 10%, 0.5% to 10%, 0.6% to 10%, 0.7% to 10%, 0.8% to 10%, 0.9% to 10%, 1.0% to 10%, or 1.0% to 9%, weight per weight of extract.

In embodiments where the composition comprises 6-gingerol, the amount of 6-gingerol in the composition may, in some embodiments, be in the range of from about 2% to 40%, 5% to 40%, 6% to 35%, 7% to 30%, 8% to 30%, 9% to 25%, or 10% to 20%, weight per weight of composition.

In embodiments where the composition comprises 6-gingerdione, the amount of 6-gingerdione in the composition may, in some embodiments, be in the range of from about 0.2% to 10%, 0.2% to 8%, 0.2% to 7%, 0.3% to 6%, 0.3% to 5%, or 0.4% to 5%, weight per weight of composition.

In embodiments where the composition comprises 8-gingerdione, the amount of 8-gingerdione in the composition may, in some embodiments, be in the range of from about 0.02% to 10%, 0.05% to 8%, 0.1% to 7%, 0.2% to 6%, 0.3% to 6%, 0.4% to 6%, 0.5% to 6%, 0.6% to 6%, or 0.5% to 5%, weight per weight of composition.

In embodiments where the composition comprises 10-gingerol, the amount of 10-gingerol in the composition may, in some embodiments, be in the range of from about 0.15% to 10%, 0.2% to 9%, 0.3% to 8%, 0.4% to 7%, 0.5% to 7%, 0.6% to 7%, 0.7% to 7%, 0.8% to 7%, 0.9% to 7%, 1% to 7%, 1% to 6%, 1% to 5%, 1.5% to 5%, 2% to 5%, 2% to 6%, or 2% to 7%, weight per weight of composition.

In embodiments where the composition comprises 10-shogaol, the amount of 10-shogaol in the composition may, in some embodiments, be in the range of from about 0.04% to 3%, 0.04 to 2%, 0.05% to 2%, 0.06% to 2%, 0.1% to 1.5%, 0.2% to 1.5%, 0.06 to 1.5%, or 0.06% to 1%, weight per weight of composition.

In embodiments where the composition comprises 6-gingerdiol, the amount of 6-gingerdiol in the composition may, in some embodiments, be in the range of from about 0.25% to 5%, 0.25% to 4%, 0.25% to 3%, or 0.3% to 3%, weight per weight of composition.

In embodiments where the composition comprises 6-shogaol, the amount of 6-shogaol in the composition may, in some embodiments, be in the range of from about 0.2% to 10%, 0.25% to 9%, 0.3% to 8%, 0.4% to 7%, 0.5% to 6%, 0.6% to 5%, 0.7% to 5%, 0.2% to 5%, or 0.2 to 6%, weight per weight of composition.

In embodiments where the composition comprises 8-gingerol A, the amount of 8-gingerol A in the composition may, in some embodiments, be in the range of from about 0% to 10%, 0% to 8%, 0% to 7%, 0.01 to 6%, or 0.01% to 5%, weight per weight of composition.

In embodiments where the composition comprises 8-gingerol B, the amount of 8-gingerol B in the composition may, in some embodiments, be in the range of from about 0% to 10%, 0% to 8%, 0% to 7%, 0.01 to 6%, or 0.01% to 5%, weight per weight of composition.

In one embodiment, the topical composition further comprises one or more volatile compounds. In one embodiment, the area % ratio of volatile to non-volatile compounds in the composition is in the range of from 0.02 to 44.0, 0.1 to 44.0, 0.2 to 44.0, 0.02 to 40.0, 0.1 to 40.0, 0.5 to 40.0, 0.02 to 35, 0.05 to 35.0, 0.1 to 35.0, 1.0 to 35.0, 0.05 to 30.0, 0.1 to 30.0, 1.0 to 30.0, 0.05 to 25.0, 0.1 to 25.0, 0.5 to 25.0, 1.0 to 25.0, 0.05 to 20.0, 0.1 to 20.0, 0.5 to 20.0, 1.0 to 20.0, 0.05 to 18.0, 0.1 to 18.0, 0.5 to 18.0, 1.0 to 18.0, 0.05 to 15.0, 0.1 to 15.0, 0.5 to 15.0, 1.0 to 15.0, 2.0 to 40.0, 2.0 to 35.0, 2.0 to 30.0, 2.0 to 25.0, 2.0 to 20.0, 2.0 to 15.0, 3.0 to 40.0, 3.0 to 35.0, 3.0 to 30.0, 3.0 to 25.0, 3.0 to 20.0, or 3.0 to 15.0. Typically, the area % is as determined by GCFID.

In one embodiment, the topical composition comprises:
(a) gingerols, gingerdiones and gingerdiols in an amount in the range of from 2.5% to 50%, 5% to 50%, 10% to 50%, 15% to 50%, 15% to 45%, 15% to 40%, or 15% to 35%, weight per weight of composition;
(b) shogaols in an amount in the range of from 0.3% to 7%, 0.3% to 6%, 0.3% to 5%, 0.4% to 5%, 0.4% to 4%, 0.5% to 4%, 0.7% to 4%, 0.8% to 3.5%, 0.9% to 3.0%, or 1% to 4%, weight per weight of composition; and
(c) volatile and non-volatile compounds in an amount to give an area % ratio of volatile to non-volatile compounds in the range of from 0.02 to 44.0, 0.1 to 44.0, 0.2 to 44.0, 0.02 to 40.0, 0.1 to 40.0, 0.5 to 40.0, 0.02 to 35, 0.05 to 35.0, 0.1 to 35.0, 1.0 to 35.0, 0.05 to 30.0, 0.1 to 30.0, 1.0 to 30.0, 0.05 to 25.0, 0.1 to 25.0, 0.5 to 25.0, 1.0 to 25.0, 0.05 to 20.0, 0.1 to 20.0, 0.5 to 20.0, 1.0 to 20.0, 0.05 to 18.0, 0.1 to 18.0, 0.5 to 18.0, 1.0 to 18.0, 0.05 to 15.0, 0.1 to 15.0, 0.5 to 15.0, 1.0 to 15.0, 2.0 to 40.0, 2.0 to 35.0, 2.0 to 30.0, 2.0 to 25.0, 2.0 to 20.0, 2.0 to 15.0, 3.0 to 40.0, 3.0 to 35.0, 3.0 to 30.0, 3.0 to 25.0, 3.0 to 20.0, or 3.0 to 15.0.

In one embodiment, the topical composition comprises:
(a) gingerols, gingerdiones and gingerdiols in an amount to give an area % in the range of from 0.04 to 2, 0.04 to 1.8, 0.04 to 1.5, 0.1 to 1.5;
(b) shogaols in an amount to give an area % in the range of from 0.90 to 20, 0.94 to 18, 0.94 to 16, 0.94 to 15, 0.94 to 14, 1.0 to 13, 1.5 to 13, 2.0 to 13, 2.5 to 13, 3.0 to 13, 3.5 to 13, 3.0 to 14, 3.0 to 15, 3.0 to 16; and
(c) volatile and non-volatile compounds in an amount to give an area % ratio of volatile compounds to non-volatile compounds in the range of from 0.02 to 44.0, 0.1 to 44.0, 0.2 to 44.0, 0.02 to 40.0, 0.1 to 40.0, 0.5 to 40.0, 0.02 to 35, 0.05 to 35.0, 0.1 to 35.0, 1.0 to 35.0, 0.05 to 30.0, 0.1 to 30.0, 1.0 to 30.0, 0.05 to 25.0, 0.1 to 25.0, 0.5 to 25.0, 1.0 to 25.0, 0.05 to 20.0, 0.1 to 20.0, 0.5 to 20.0, 1.0 to 20.0, 0.05 to 18.0, 0.1 to 18.0, 0.5 to 18.0, 1.0 to 18.0, 0.05 to 15.0, 0.1 to 15.0, 0.5 to 15.0, 1.0 to 15.0, 2.0 to 40.0, 2.0 to 35.0, 2.0 to 30.0, 2.0 to 25.0, 2.0 to 20.0, 2.0 to 15.0, 3.0 to 40.0, 3.0 to 35.0, 3.0 to 30.0, 3.0 to 25.0, 3.0 to 20.0, or 3.0 to 15.0.

Typically, the area percent of volatile compounds is the area percent of the compounds camphene, limonene, β-phellandrene, 1,8 cineole, linalool, borneol, α-terpineol, geraniol, neral, geranial, geranyl acetate, α-zingiberene, ar-curcumene, trans α-farnesene, β-bisabolene, trans muurola 4,5 diene, β-sesquiphellandrene, and zingiberenol.

Typically, the area percent of non-volatile compounds is the area percent of the compounds 6-gingerol, 8-gingerol A, 8-gingerol B, 6-gingerdiol, 6-gingerdoine, 10-gingerol, 12-gingerol, 8-gingerdione, 6-shogaol, 8-shogoal, 10-shogaol, zingerone and 6-paradol.

Typically the area % is as determined by GCFID.

In one embodiment, the topical composition further comprises 6-paradol. In embodiments where the composition comprises 6-paradol, the amount of 6-paradol in the composition may, in some embodiments, be in the range of from about 0.05% to 3%, 0.05% to 2.5%, 0.05% to 2%, 0.05% to 1.5%, 0.05% to 1.4%, or 0.05% to 1.3%, area % of the composition.

In one embodiment, the topical composition further comprises zingerone. In embodiments where the extract comprises zingerone, the amount of zingerone in the extract may, in some embodiments, be in the range of from about 0.1% to 1.5%, 0.1% to 1.3%, 0.1 to 1.2%, 0.2 to 1.2% area % of the composition.

The components of the topical composition can be obtained in isolated form from, for example, Sigma-Adlrich Inc. (St. Louis, Mo., USA)

The topical composition may include a pharmaceutically acceptable carrier as described herein.

In some embodiments, the topical compositions described herein may be in the form of ointments, pastes, creams, lotions, gels, solutions or patches. In certain embodiments, the compositions are creams, which may further contain saturated or unsaturated fatty acids such as steaeric acid, palmitic acid, oleic acid, palmato-oleic acid, acetyle, or aryl oleyl alcohols, stearic acid. Creams may also contain a non-ionic surfactant, for example, polyoxy-40-stearate.

The present invention further provides a method of treating or preventing pain, or a condition associated with pain, in a subject in need thereof, comprising applying topically an effective amount of the topical composition described herein.

Further provided is the use of a topical composition as described herein in the manufacture of a medicament for treating or preventing pain, or a condition associated with pain, in a subject in need thereof, wherein the medicament is for topical administration, or a topical composition as described herein for use in treating or preventing pain, or a condition associated with pain, in a subject in need thereof, wherein the topical composition is for topical administration.

In one embodiment, the pain is migraine.

As used herein, "treating" means affecting a subject, tissue or cell to obtain a desired pharmacological and/or physiological effect and includes inhibiting the condition, i.e. arresting its development; or relieving or ameliorating the effects of the condition i.e., cause reversal or regression of the effects of the condition. As used herein, "preventing" means preventing a condition from occurring in a cell or subject that may be at risk of having the condition, but does not necessarily mean that condition will not eventually develop, or that a subject will not eventually develop a condition. Preventing includes delaying the onset of a condition in a cell or subject. In one embodiment, treating achieves the result of relieving pain in the recipient subject. In one embodiment, preventing achieves the result of preventing the onset of pain in a recipient subject.

As used herein, the term "subject" refers to a mammal such as a human. Typically, the mammal is a human.

Another aspect of the invention provides an article of manufacture comprising an extract of Zingiber officinale and a device for topical administration of the extract. In one embodiment, the device comprises a dispenser for topical administration of the extract. In one embodiment, the dispenser is a roll-on dispenser for rolling application of the extract. In one embodiment, the device is a transdermal patch. The transdermal patch may include a reservoir layer that contains the extract or composition, an adhesive portion for adhering to the skin of the subject around the affected area, a backing portion for handling the transdermal patch, and an occlusive layer that may facilitate increasing the humidity around the application site, thereby facilitating the increase of transdermal absorption of the active ingredients.

As used herein, an "effective amount" is an amount sufficient to produce a desired effect. For example, an effective amount may be an amount sufficient to treat or prevent pain.

Another aspect of the invention provides a method of extracting a substance from a raw material, comprising combining the raw material with solvent at a temperature in the range of from 293.15K to 313.15K and a pressure in the range of from 10 to 25 MPa. Typically, the solvent is $CO_2$. In one embodiment, the solvent and raw material are combined in a weight ratio (S/F ratio) of 20 to 1, 19 to 1, 18 to 1, 17 to 1, 16 to 1, 15 to 1, 14 to 1, 13 to 1, 12 to 1, 11 to 1, 10 to 1, 9 to 1, 8 to 1, 7 to 1 solvent to raw material. Typically, the S/F ratio is 15 to 1.

In one embodiment, the temperature is 313K and the pressure is 20 MPa.

In one embodiment, the raw material is from Zingiber officinale (ginger), such as Zingiber officinale rhizome. Typically, the Zingiber officinale is dried. Typically, the raw material is ground dried Zingiber officinale.

All publications mentioned in this specification are herein incorporated by reference. It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The disclosure will now be described by way of reference only to the following non-limiting examples. It should be understood, however, that the examples following are illustrative only, and should not be taken in any way as a restriction on the generality of the invention described herein.

EXAMPLES

Example 1: Preparation of Zingiber officinale Extract

Sliced or whole Zingiber officinale rhizome was dried in 2 continuous drying drums. Raw sliced or whole ginger was rotated in a first drum with air input at a temperature of 80° C. until the ginger was semi dried. The semi dried ginger was then transferred to a second rotating drum with air input at a temperature of 63° C. until a moisture content of less than or equal to 12% was obtained.

The dried rhizome was then ground into a course powder. Subcritical extracts were prepared by placing the dried rhizome into the extraction chamber of a Subcritical Extractor (D.D.F. (Australia) Pty Ltd) and extracting the rhizome with $CO_2$ at a temperature of from 25° C. to 28'C and a pressure of from 6.5 to 6.8 MPa. Supercritical extracts were prepared by placing the dried rhizome into the extraction chamber of a Supercritical Extractor and extracting the rhizome at a temperature of 293.15~313.15K and a pressure of 10~25 MPa.

TABLE 1

Experimental conditions and extraction yields for the ginger extraction with CO2 as solvent and hydrodistillation.

| Run | Solvent | T (K) | P (MPa) | Density[d] (kg m$^{-3}$) | Extraction yield[a] | Time of extraction (min) | Extraction percent (wt %)[b] |
|---|---|---|---|---|---|---|---|
| 1 | $CO_2$ | 293.15 | 10.00 | 856.21 | 1.68 | 180 | 93.85 |
| 2 | $CO_2$ | 293.15 | 25.00 | 964.10 | 1.90 | 180 | 106.14 |
| 3 | $CO_2$ | 333.15 | 10.00 | 289.53 | 0.24 | 180 | 13.41 |
| 4 | $CO_2$ | 333.15 | 25.00 | 788.70 | 2.62 | 180 | 146.37 |
| 5[c] | $CO_2$ | 313.15 | 17.50 | 814.68 | 1.88 (±0.09) | 180 | 105.03 |
| 7 | Hydro-distillation | ≅370.15 | ≅94 × 10$^{-3}$ | — | 1.79 (±0.10) | 180 | 100.00 |

[a](Mass of extract per mass of dried material) × 100.
[b](Mass of extract obtained with the pressurized solvent at the end of extraction period per mass of oil extracted using hydrodistillation × 100.
[c]Average value and standard deviation of triplicate runs.
[d]CO2 densities were obtained from Angus et al. (1976) International Tables of the Fluid State, vol. 3, Carbon Dioxide, Pergamon Press, Oxford.

The highest yields obtained for the ginger extracts were 26.2 g extract/kg ginger using super-critical $CO_2$ at 25.0 MPa and 333.15 K. In the case of supercritical CO the pressure and temperature have a positive effect on the yield.

Regarding the effects of pressure and temperature on the composition of the extracts obtained in this work using CO2 as the solvent, the results show that, with the exception of geranial and zingiberene, the compounds were present in the extracts in higher mass fraction when the extraction conditions of lower temperature and pressure (Run 1) were applied.

The resulting extracts were assessed by NMR, FTIR and GCFID for content and were subsequently tested on subjects for efficacy.

Example 2: Analysis of *Zingiber Officinale* Extracts

Nuclear Magnetic Resonance (NMR), Fourier Transform Infrared (FTIR) and Gas Chromatography (GC) Mass Spectrometric analysis were conducted on 4 subcritical extracts and 1 supercritical extract of *Zingiber officinale*, and the results compared.

Subcritical (A, B, D and E) and supercritical extracts (C) were dissolved in $CDCl_3$ and analysed by NMR. Levels of gingerol were determined by comparison of the gingerol signal (methoxy signal a in formula 1 below) to an internal Eretic NMR spike. The molecular weight of 6-gingerol was used for mass calculation.

In addition to NMR, each sample was diluted 1:100 in absolute ethanol and an aliquot of the solution analysed by GC-MS to identify any volatile components present using a mass spectral library.

The results of the analysis are shown in Table 2. Table 3 shows a summary of the gingerol and shogaol levels in the extracts produced from Example 1. Subcritical $CO_2$ extracts are designated A (N11808-1), B (N11808-2), D (N11879-1) and E (N11931-1). C (N11808-3) is a supercritical $CO_2$ extract.

The structure of gingerols and shogaol is shown below with the individual protons labeled a to h (in gingerol) and i and j in shogaol.

Gingerols:

wherein n is 1, 2, 3.
Shogaol:

TABLE 2

| No. | Chemical Shift | Protons identified/ Comment | % of total components detected | | | | |
|---|---|---|---|---|---|---|---|
| | | | A | B | C | D | E |
| 9 | ~10.2-9.2 | Phenols/acids suspected | 0.27 | 0.35 | 0.13 | 0.19 | 0.92 |
| 8 | ~7.6-7.0 | Aromatics | 0.49 | 1.15 | 1.25 | 0.84 | 0.83 |
| 7 | ~7.0-6.6 | Gingerol b, c, d, Shogaol i | 3.71 | 3.04 | 0.80 | 3.34 | 2.91 |
| 6 | ~6.6-6.2 | Unsaturation - terpene | 0.79 | 0.79 | 0.83 | 0.64 | 0.66 |
| 5 | ~6.2 | Shogaol j | 0.16 | 0.21 | 0.08 | 0.1 | 0.06 |
| 4 | ~6.4 | Unsaturation - terpene and gingerol h | 9.14 | 11.75 | 12.75 | 10.83 | 10.34 |
| 3 | ~4-3.8 | Gingerol methoxy a | 3.70 | 3.40 | 0.77 | 3.20 | 3.83 |
| 2 | ~3-2.75 | Gingerol e | 4.71 | 3.98 | 2.20 | 4.62 | 3.98 |
| | ~2.75-0.5 | Aliphatic contains terpene and alkyl side chain of gingerol. including f | 77.03 | 75.39 | 81.21 | 76.24 | 77.16 |
| 10 | ~3.8-3.2 | Not identified | — | — | — | — | 0.37 |

TABLE 3

| | A | B | C | D | E |
|---|---|---|---|---|---|
| Gingerol | 8% | 12-24 | 8% | 14% | ~12.6% |
| Shogaol* | ~0.7% | ~1-3% | ~0.6% | ~1.3% | ~0.7% |

+ based on magnitude of signal ratios

NMR results show that gingerols and shogaols are present in both subcritical and supercritical extracts of dried *Zingiber officinale*. The concentration of gingerols (by signal ratio comparison) in extracts obtained by subcritical $CO_2$ extraction was higher than obtained by supercritical $CO_2$ extraction. The supercritical extraction had a higher ratio of non-gingerol to gingerol components.

GC indicated the presence of terpenes such as Zingiberene and Farnesene, gingerol and shogaol. The supercritical extraction sample had a higher ratio of terpene to gingerol.

FTIR analysis also indicated that supercritical extracts had a higher ratio of terpene to gingerol.

Example 3: Treatment of Migraine Pain 5 ml aliquots of *Zingiber officinale* extract prepared by subcritical $CO_2$ extraction as described above were dispensed into bottles having a roll-on applicator. 19 subjects who were prone to suffering from migraine pain were each given a roll-on applicator containing the extract, and each subject applied 6 rolls of the extract across the forehead following onset of migraine pain.

100% of subjects reported significant relief of migraine pain within 60 minutes of application of the extract, with 89% of subjects reporting total relief of migraine pain some of the time, and 37% of subjects reporting total relief of migraine pain 100% of the time. 37% of subjects also reported total relief and lower incidence of migraine pain.

Example 4: Treatment of Arthritis and Period Pain

Topical application of the extract to the knee of a subject suffering from arthritis of the knee resulted in significant relief of arthritis pain.

Topical application of the extract to the stomach of a woman suffering from menstrual pain resulted in significant relief of the menstrual pain.

These results indicate that extracts of *Zingiber officinale* are effective at treating a number of different types of pain or inflammation by topical administration.

Example 5: Preparation of Further Subcritical Extracts of *Zingiber officinale*

*Zingiber officinale* from the variety Queensland and Jumbo was dried and ground and as described above in Example 1. Subcritical extracts of the *Zingiber officinale* were prepared using $CO_2$ at different temperatures and/or pressures by placing the dried rhizome into the extraction chamber of a Subcritical Extractor (D.D.F. (Australia) Pty Ltd) as described in WO 09/055849. The conditions for the extraction are set out in Table 4.

TABLE 4

| | Extract | | |
|---|---|---|---|
| | F | G | H |
| Variety | Queensland | Queensland | Jumbo |
| Temperature (° C.) | 25-28 | 28 | 26 |
| Pressure (MPa) | 6.2-6.8 | 6.4 | 6.4 |

The extracts obtained under the above conditions were designated extracts F, G and H.

Example 5: Preparation of Supercritical Extracts of *Zingiber Officinale*

Figure 1:
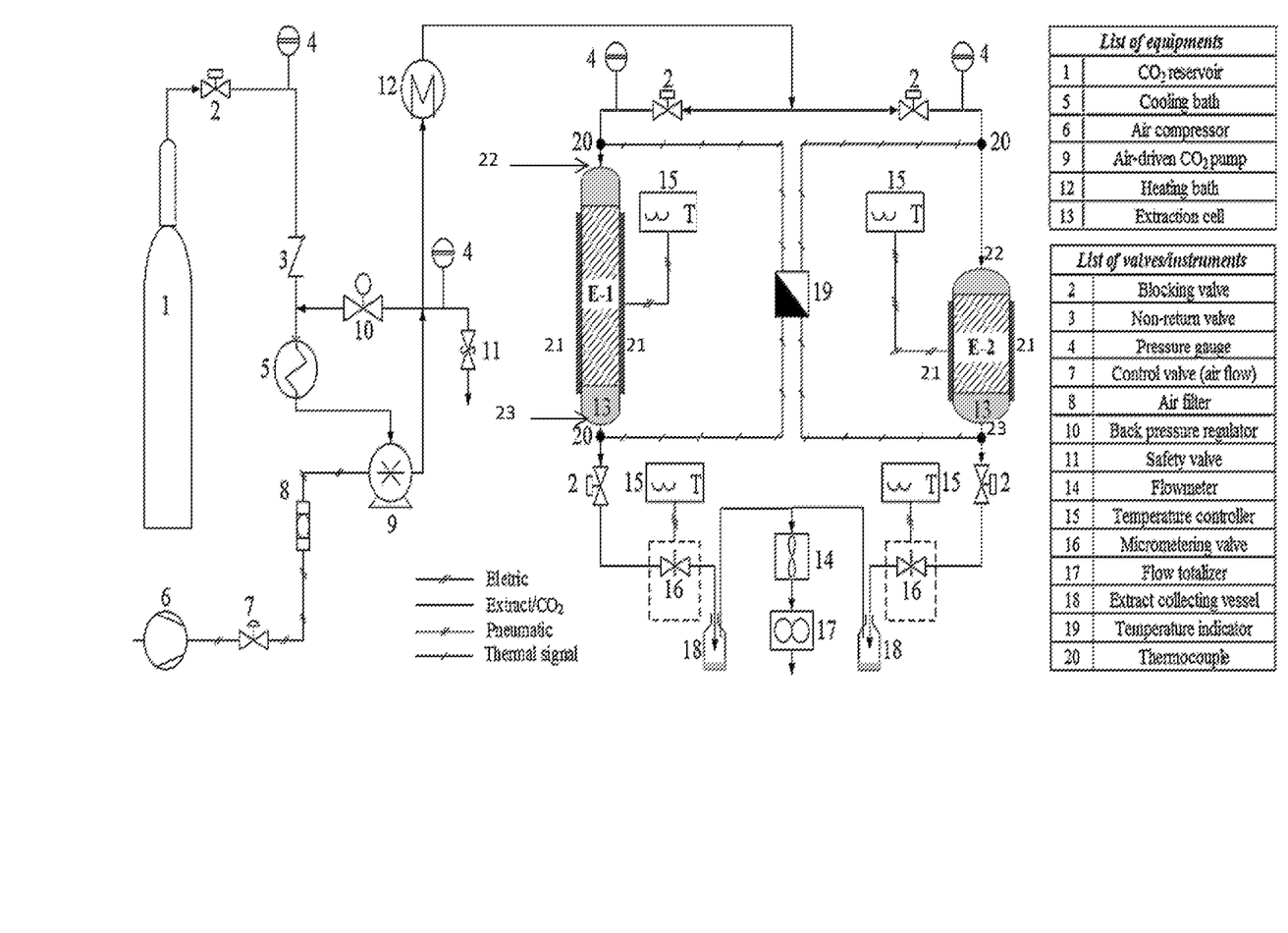
FIG. 1 is a schematic representation of an example of an arrangement of components for supercritical $CO_2$ extraction.

The rhizome of Brazilian and Queensland ginger was dried and ground as described in Example 1 except that the % moisture content of the Brazilian ginger was 19.3%. Supercritical extracts were prepared using a 0.3 Liter extractor for the Brazilian ginger, and a 1 Liter extractor for the Queensland ginger. A schematic diagram of the extraction equipment used for the extraction is shown in FIG. 1. Referring to FIG. 1, dried ginger was placed into extraction cell E-2 (13), and $CO_2$ passed through the extraction cell at the temperature, pressure and S/F ratio as set out in Table 5. In more detail, liquid $CO_2$ in $CO_2$ reservoir (1) was passed through non-return valve 3 and subsequently passed through cooling bath 5. The CO2 was then pumped by $CO_2$ pump 9 through heating bath 12 where the $CO_2$ was heated. The heated $CO_2$ was pumped from heating path 12 where it passed through inlet 22 of extraction cell 0.3. The pressure of the $CO_2$ in the extraction cell was controlled by valve 2 in conjunction with pressure gauge 4. The temperature of the extraction cell was maintained by temperature controller which was linked to heating elements 21. Extract passed through outlet 23, micrometering valve 16 and was collected in vessel 18.

The extraction cells used were SFE-2 (1 liter) from Applied Separations Allentown Pa. USA, and have the dimensions 0.212 m height and 0.078 m diameter. The parameters of the extraction are set out in Table 5.

TABLE 5

| | Brazilian ginger (I) | Queensland ginger (J) |
|---|---|---|
| Extraction unit | 0.3-L extractor | 1-L extractor |
| Moisture (%) of ginger | 19.3 | 8.4 |
| Apparent density of the bed (kg/m3) | 708.9 | 902.2 |
| Dry Ginger | 66.95 | 872.48 |
| S/F Ratio (mass of solvent/mass of ginger) | 15 | 15 |
| Extraction yield (%, dry basis) | 3.9 | 3.3 |
| Temperature | 313 K | 313 K |
| Pressure | 20 MPa | 20 MPa |

For these extractions, the solvent (S) to dry feed (F) mass ratio (S/F) was maintained at a constant 15. That is, a quantity of solvent equal to 15 times the mass of raw material was used. Maintaining the same S/F ratio ensures that the same amount of solvent is used in different extraction beds because it is not influenced by solvent flow variation.

The above extracts for Brazilian ginger was designated I and the above extract for Queensland ginger was designated J.

In addition to the above extracts, an extract from Indian ginger was prepared using the supercritical method described in Example 5 (designated Indian), and a further extract was prepared using the subcritical method described in Example 5 (designated K).

Extracts F, G, H, I, J, K and Indian were assessed for their ability to prevent or treat migraine, and analyses by GCFID and HPLC for their content, as described below.

Example 6: Assessment of Efficacy of Subcritical and Supercritical Extracts of *Zingiber officinale*

The extracts F, G, H, I, J, K and Indian were assessed for their ability to prevent or reduce migraine.

1 ml aliquots of *Zingiber officinale* extract F prepared by subcritical $CO_2$ extraction as described above were dispensed into 3 ml bottles having a roll-on applicator. 27 subjects who were prone to suffering from migraine pain were each given a roll-on applicator containing the extract, and each subject applied 6 rolls of the extract across the forehead following onset of prodrome migraine symptoms, such as aura.

23 subjects, of which 21 were female and 2 male, reported their results daily. Of the 23 subjects, 21 followed the recommended protocol of applying the *Zingiber officinale* extract at their first sign of prodrome migraine symptoms. Of these 100% of female subjects reported stopping migraine with the topical application, and overall 95% of test subjects reported stopping migraine with the topical application. The results with extract F are set out in Table 6.

TABLE 6

| Description | Result |
| --- | --- |
| Qualified Participants | 27 |
| Lost contact | 4 |
| Opportunity Set | 23 |
| Of Which Female | 21 |
| Of Which Male | 2 |
| Experienced Stopping a Migraine | 18 |
| Non Compliant | 2 |
| Experienced Stopping a Migraine & Compliant | 95% |
| Experienced Stopping a Migraine & Compliant & Female | 100% |

1 ml aliquots of *Zingiber officinale* extracts G, H, I, J, K and Indian were subsequently supplied to the 3 most chronic migraine sufferers as a comparison for efficacy against Extract F. Extracts G, H, I, J and K all exhibited efficacy in preventing or reducing migraine. The Indian extract was shown to have the least efficacy, with only limited reduction or prevention of migraine. The results are summarized in Table 7.

Extracts H and J had improved patient acceptance as compared to original extract F or the other two Extracts G and I. During the trial period 100% relief from migraines were reported for extracts H and J. Extracts H and J were also reported to have stronger anti-nausea benefits.

TABLE 7

| Extract | Efficacy* |
| --- | --- |
| F | 4/4 |
| G | 3/4 |
| H | 4/4 |
| I | 2/4 |
| J | 4/4 |
| K | 3/4 |
| Indian | 1/4 |

*efficacy was assessed with 4 representing 100% relief from migraine and 0 representing no relief from migraine.

Example 7: Analysis of *Zingiber officinale* Extracts

The non-volatile components of extracts F, G, H, I, J, K and India were assessed using High Performance Liquid Chromatography. A stock solution of reference standards was prepared by dissolving 5 mg of reference standard (Sigma-Aldrich) in 5 ml of methanol. A serial dilution of each standard was prepared to create a five-point standard curve. Samples were run using an Agilent 1100, DAD Detector and a Phenomenex Synergi C18, 4 μm, 250 mm×4.6 mm column. Values of w/w % were calculated for test samples using a linear regression formula generated from the standard curve using the HPLC instrument software. The results of HPLC are shown in Table 8.

TABLE 8

| HPLC Assay | K | F | G | H | J | I | Indian |
| --- | --- | --- | --- | --- | --- | --- | --- |
| Efficacy | 3/4 | 4/4 | 3/4 | 4/4 | 4/4 | 2/4 | 1/4 |
| | % w/w | % w/w | % w/w | % w/w | % w/w | % w/w | % w/w |
| 6-gingerol | 15.50 | 11.71 | 13.08 | 11.23 | 17.15 | 14.77 | 1.35 |
| 8-gingerol A | 2.64 | 2.50 | 0.04 | 1.29 | 3.14 | 2.31 | 0.17 |
| 8-gingerol B | 0.04 | 0.05 | 2.24 | 0.02 | 0.04 | 0.06 | 0.47 |
| 6-gingerdiol | 1.74 | 2.04 | 0.50 | 0.34 | 0.45 | 0.37 | 0.23 |
| 6-gingerdione | 0.45 | 0.52 | 3.45 | 1.67 | 3.47 | 3.31 | 0.18 |
| 10-gingerol | 3.72 | 3.23 | 3.11 | 1.76 | 4.62 | 3.62 | 0.11 |
| 12-gingerol | 0.00 | 0.00 | 0.11 | 0.03 | 0.12 | 0.12 | 0.00 |
| 8-gingerdione | 0.70 | 0.73 | 3.76 | 0.47 | 4.61 | 3.69 | 0.01 |
| Total Gingerols & gingerdiones | 24.78 | 20.77 | 26.29 | 16.81 | 33.60 | 28.25 | 2.51 |
| 6-shogaol | 2.41 | 0.92 | 4.31 | 2.67 | 2.00 | 0.28 | 1.27 |
| 8-shogaol | 0.45 | 0.20 | 0.65 | 0.36 | 0.43 | 0.14 | 0.43 |
| 10-shogaol | 0.64 | 0.30 | 0.74 | 0.33 | 0.43 | 0.07 | 0.03 |
| Total shogaols | 3.49 | 1.42 | 5.71 | 3.37 | 2.86 | 0.49 | 1.73 |

The results show that extracts which are most effective at treating or preventing migraine have higher amounts of gingerols, gingerdiones and shogaols compared to an extract having low efficacy. In this regard, all extracts showing higher efficacy had higher amounts of 6-gingerol, 6-gingerdione, 6-gingerdiol, 10-gingerol and 10-shogaol than extract with low (¼) efficacy.

The volatile and non-volatile components of extracts F, G, H, I, J, K and Indian were analysed by Gas chromatography with flame ionization detector (GCFID) (such as an Agilent 6980 gas chromatograph, with separation performed on a 50 m×320 μm id×1.05 μm HP-5 column (Agilent), with helium as a carrier gas at about 85 kPa, and temperature program 50° C. to 280° C. at 2° C./min) to determine the compounds present in these extracts. 1 μl of sample was dissolved in 1 ml of 98% ethanol or 10 mg of sample dissolved in 10 ml HPLC grade acetone. The dissolved sample was injected into the GCFID and the retention time, peak area, and percent area determined, in conjunction with ISO, BP or USO guidance for essential oils, from the GC report. The results of the analysis are shown in Table 9.

TABLE 9

| | EXTRACT | K | F | G | H | J | I | Indian |
|---|---|---|---|---|---|---|---|---|
| Volatiles | Efficacy | 3/4 | 3/4 | 3/4 | 4/4 | 4/4 | 2/4 | 1/4 |
| | Camphene | 3.05 | 2.08 | 0.99 | 1.44 | 2.52 | 0.12 | 0.36 |
| | Limonene | | | 0.45 | 0.69 | 0.90 | 0.19 | 0.3 |
| | β-phellandrene | 2.68 | 2.34 | 1.10 | 1.00 | 3.40 | 0.65 | 0.58 |
| | L 8 cineole | 1.82 | 1.32 | 1.14 | 2.01 | 1.53 | 0.59 | 0.89 |
| | Linalool | | | 0.38 | 0.46 | 0.41 | 0.35 | 0.48 |
| | Borneol | 1.02 | | 0.61 | 0.76 | 0.64 | 0.50 | 1.07 |
| | α-terpineol | | | 0.50 | 0.67 | 0.45 | 0.39 | 0.56 |
| | Geraniol | | | 1.07 | 1.29 | 1.18 | 0.58 | |
| | Neral | 1.22 | 3.35 | 0.61 | 1.75 | 1.74 | 2.57 | |
| | Geranial | 2.03 | 6.33 | 1.02 | 2.96 | 3.19 | 4.03 | |
| | Geranyl acetate | | 2.14 | 2.64 | 0.72 | 1.69 | 0.25 | |
| | α-zingiberene | 27.49 | 23.52 | 20.49 | 11.67 | 19.92 | 23.80 | 28.98 |
| | Ar-curcumene | 11.05 | 12.94 | 15.34 | 12.18 | 12.24 | 12.05 | 19.89 |
| | Trans, trans α-farnesene | 5.09 | 4.16 | 5.03 | 4.37 | 4.11 | 3.89 | 7.51 |
| | β-bisabolene | 2.82 | 2.33 | 3.00 | 2.63 | 2.19 | 2.28 | 4.29 |
| | Trans munrola 4,5 diene | | | 1.00 | 0.76 | 0.88 | 0.85 | 1.46 |
| | β-sesquiphellandrene | 10.61 | 8.36 | 9.79 | 7.72 | 8.67 | 8.85 | 13.8 |
| | Zingiberenol | 0.57 | 0.48 | 0.90 | 0.97 | 0.52 | 0.67 | 0.46 |
| | Total Area % volatiles | 69.45 | 69.35 | 66.06 | 54.05 | 66.18 | 62.61 | 80.63 |
| Non-volatiles | Trans-6-shogaol | 3.37 | 2.27 | 5.58 | 7.25 | 3.23 | 1.03 | 0.86 |
| | Gingerols | 0.42 | 0.21 | 0.61 | 0.34 | 1.10 | 1.05 | 0.04 |
| | Trans-8-shogaol | 0.66 | 0.44 | 0.93 | 1.22 | 0.69 | 0.30 | 0.08 |
| | Trans-8-dihydro shogaol | 0.64 | 0.90 | 1.12 | 3.36 | 1.39 | 1.56 | |
| | Trans 10-shogaol | 0.58 | 0.47 | 0.86 | 0.45 | 1.51 | 2.46 | |
| | 6-paradol | 0.09 | 0.51 | 0.66 | 1.14 | 0.61 | 0.76 | 0.16 |
| | Zingerone | 0.31 | 0.22 | 1.07 | 1.00 | 0.65 | 0.29 | 0.69 |
| | Total Area % non-volatiles | 6.07 | 5.02 | 10.83 | 14.76 | 9.18 | 7.45 | 1.83 |

The area % ratio of volatile compounds to non-volatile compounds was calculated from the GCFID data for extracts Indian, F, G, H, I, J and K as well as for extracts that were obtained from Queensland Zingiber officinale under very high pressure (L). The ratio of the area % of volatile to non-volatile compounds was determined by dividing the total area % for volatile compounds with the total area % for non-volatile compounds, as determined by GCFID (Table 9).

The ratio of the area % volatile to weight % non-volatile was calculated by dividing the total area % of volatile compounds determined by GCFID (Table 9) with the total weight per weight percent for the non-volatile compounds determined by HPLC (Table 8).

The results are summarised in Table 10.

TABLE 10

| Extract | Indian | K | I | G | P | J | H | L |
|---|---|---|---|---|---|---|---|---|
| Efficacy rating out of 4 | 1 | 3 | 2 | 3 | 4 | 4 | 4 | Very Hot Blistered skin |
| Area % Ratio volatile/non volatile compounds | 44.06 | 11.44 | 8.40 | 6.10 | 13.82 | 7.21 | 3.66 | 0.02 |
| Area % volatile/% w/w non volatile compounds | 19.02 | 2.46 | 2.18 | 2.06 | 3.13 | 1.82 | 2.68 | |

The results showed that extracts of Zingiber officinale having the most efficacy had an area % ratio of volatile to non-volatile in the range of from 3.0 to 15. The extract with the least efficacy in the treatment of migraine had an area % ratio of 44.06. An extract having an area % ratio of 0.02 was corrosive to the skin. Extracts having no non-volatile components showed no efficacy (data not shown).

Without wishing to be bound by theory, the inventor believes that non-volatile components in the extract (such as gingerols, gingerdiones and shogaols) are necessary for the efficacy of the extract, while volatile components, such as essential oils, serve at least in part to reduce the caustic effects of the non-volatile components.

Whilst specific embodiments of a method and composition for treating or preventing pain have been described, it should be appreciated that the method and composition may be embodied in other forms.

For example, the extract may be formulated with pharmaceutically acceptable carriers or excipients.

In the claims which follow, and in the preceding description, except where the context requires otherwise due to express language or necessary implication, the word "comprise" and variations such as "comprises" or "comprising" are used in an inclusive sense, i.e. to specify the presence of the stated features but not to preclude the presence or addition of further features in various embodiments of the method and composition as disclosed herein.

The invention claimed is:

1. A method of treating migraine pain, or a condition associated with migraine pain, in a subject in need thereof, comprising applying topically to the subject an effective amount of a composition comprising a solvent extract of *Zingiber officinale*, wherein the solvent extract comprises volatile and non-volatile compounds from the *Zingiber officinale*, wherein the composition comprises from about 0.3 to about 7% w/w shogaols, and wherein the solvent extract is the only active ingredient in the composition.

2. The method of claim 1, wherein the solvent is $CO_2$.

3. The method of 1, wherein the solvent extract is a subcritical $CO_2$ extract of *Zingiber officinale*.

4. The method of claim 1, wherein the solvent extract is a supercritical $CO_2$ extract of *Zingiber officinale*.

5. The method of claim 1, wherein the solvent extract is an extract of *Zingiber officinale* rhizome.

6. The method of claim 1, wherein the composition comprises from about 2% to about 40% gingerol.

7. The method of claim 1, wherein the composition comprises from about 0.2% to about 10% gingerdiones.

8. The method of claim 1, wherein the composition comprises an area % ratio of volatile compounds to non-volatile compounds in the range of from 3.0 to 15.

9. A method of treating migraine pain, or a condition associated with migraine pain, in a subject in need thereof, comprising applying topically to the subject an effective amount of a composition comprising from 50% to 100% of a subcritical and/or supercritical $CO_2$ extract of *Zingiber officinale*, wherein the $CO_2$ extract comprises volatile and non-volatile compounds from the *Zingiber officinale*, wherein the $CO_2$ extract comprises from about 0.3 to about 7% shogaol, and wherein the $CO_2$ extract is the only active ingredient in the composition.

10. The method of claim 9, wherein the extract comprises an area % ratio of volatile compounds to non-volatile compounds in the range of from 3.0 to 15.

11. A method of treating migraine, or a condition associated with migraine, in a subject in need thereof, comprising applying topically to the subject an effective amount of a composition comprising a subcritical and/or supercritical $CO_2$ extract of *Zingiber officinale*, wherein the $CO_2$ extract comprises from about 0.3 to about 7% shogaol, and wherein the $CO_2$ extract is the only active ingredient in the composition.

12. The method of claim 11, wherein the composition comprises an area % ratio of volatile compounds to non-volatile compounds in the range of from 3.0 to 15.

* * * * *